United States Patent [19]

Rogers

[11] Patent Number: 5,092,874
[45] Date of Patent: Mar. 3, 1992

[54] PENETRATING KERATOPLASTY TREPHINATION PRESS

[76] Inventor: James C. Rogers, 1201 Highland Ct., Iowa City, Iowa 52240

[21] Appl. No.: 520,051

[22] Filed: May 7, 1990

[51] Int. Cl.⁵ ............................................. A61B 17/16
[52] U.S. Cl. .................................................. 606/166
[58] Field of Search .................... 606/166, 184, 107

[56] References Cited

U.S. PATENT DOCUMENTS

| | | | |
|---|---|---|---|
| 3,058,471 | 10/1962 | Shope | 606/166 |
| 4,077,411 | 3/1978 | Ward | 606/166 |
| 4,190,050 | 2/1980 | Bailey | 606/184 |
| 4,236,519 | 12/1980 | La Russa et al. | 606/166 |
| 4,319,575 | 3/1982 | Bonte | 606/166 |
| 4,416,278 | 11/1983 | Miller | 606/184 |
| 4,660,556 | 4/1987 | Swinger et al. | 606/166 |
| 4,718,420 | 1/1988 | Lemp | 606/166 |
| 4,744,362 | 5/1988 | Gründler | |

FOREIGN PATENT DOCUMENTS 0238196  8/1986  Fed. Rep. of Germany ...... 606/166

Primary Examiner—C. Fred Rosenbaum
Assistant Examiner—William Lewis
Attorney, Agent, or Firm—James C. Nemmers

[57] ABSTRACT

An instrument for facilitating the accurate trephination of donor corneal tissue. The instrument can easily accommodate different sizes of trephines and provides for proper and accurate positioning of the donor tissue to ensure a proper central cut of the tissue. The instrument utilizes an integral base and stand that supports a moveable piston which drives the trephine through the tissue carried by a cutting block supported on the base.

13 Claims, 2 Drawing Sheets

PENETRATING KERATOPLASTY TREPHINATION PRESS

BACKGROUND OF THE INVENTION

Because of the advancements that have been made in the field of medicine, there has been an increase in the transplanting of various organs from a donor to a needy patient. This has certainly been true in the field of opthomology where corneal transplants are almost routinely made. As a part of the surgical procedure involved in a corneal transplant, the donor tissue must be accurately cut into a circular button of a predetermined diameter. The diameter of the donor button will vary depending upon the size of the diseased cornea removed from the patient. At the present time, the donor tissue is cut by a hand-held trephine. If the surgeon does not precisely line up the cutting block holding the donor tissue, or if the trephine is not accurately positioned, the donor tissue may not be accurately cut and may be wasted. There is therefore a need for a device that will ensure a proper, central cut of the donor tissue and which will accommodate the wide range of trephine sizes presently in use. Such a device would not only assure a more accurate and precise cut of the donor tissue, but it would also speed up the surgical procedure. Any such device must of course be easy to use and capable of being sterilized in a autoclave or with gas.

SUMMARY OF THE INVENTION

The apparatus of the invention is comprised of a base and a single neck stand that supports a spring-activated moveable piston which will drive the trephine through the donor tissue supported on a cutting block positively positioned on the base. The piston uses as expandable collet that can accommodate trephines of any size, and because the cutting block is positively positioned on the base in alignment with the piston holding the trephine, accurate, central cuts of the donor tissue will always result.

DESCRIPTION OF THE PREFERRED EMBODIMENT OF THE INVENTION

Figure 1:
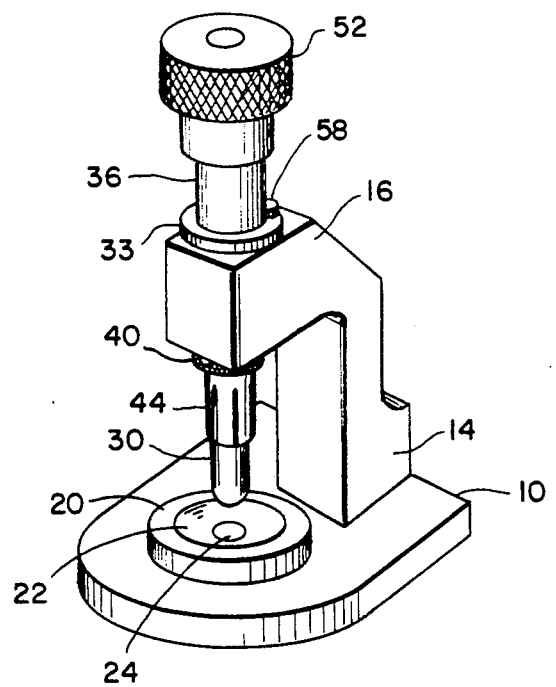
FIG. 1 is a perspective view of the assembled device of the invention.
Figure 2:
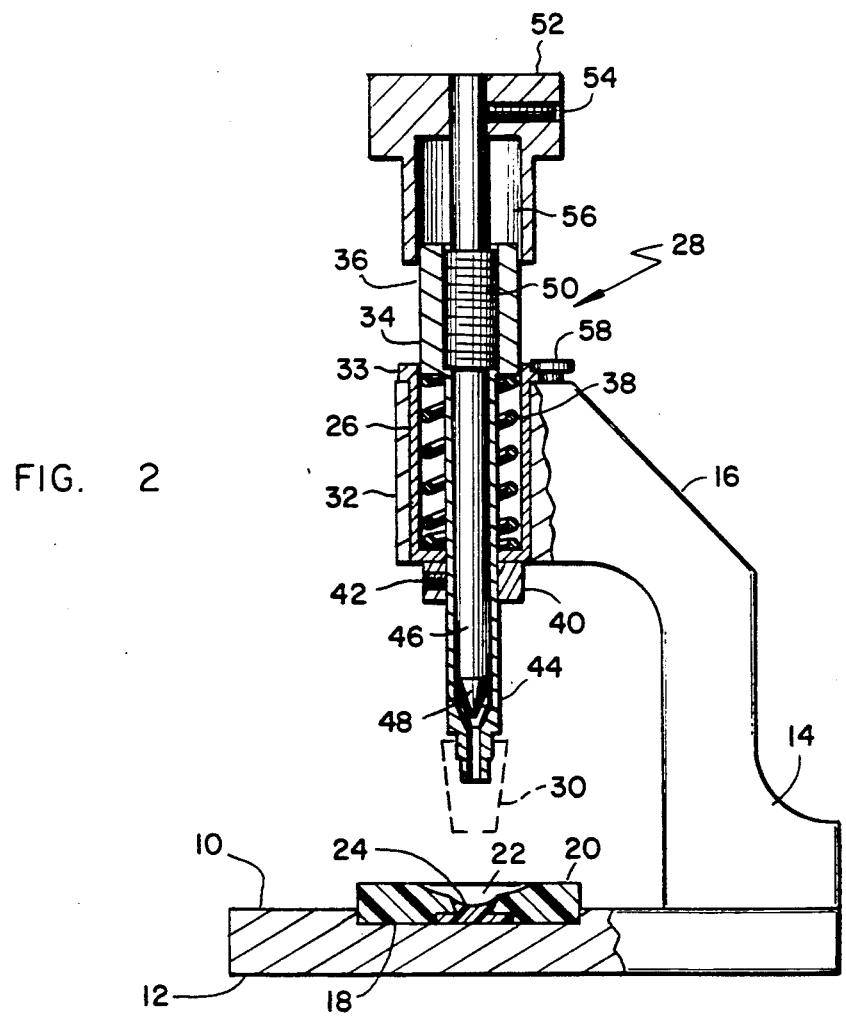
FIG. 2 is a vertical sectional view of the assembled device of the invention.

The device of the invention is a portable device and has a base 10 with a flat planar lower surface 12 so that the base 10 will rest firmly on a flat surface. Affixed to or formed as a part of base 10 is a stand 14 that has a neck 16 extending over a guide depression 18 formed in the upper surface of base 10. The depression 18 is formed and adapted to receive and position a removable cutting block 20 that is made from Teflon. The cutting block 20 contains a curved concave depression 22 in the center of its upper surface beneath which is a guide button 24 preferably formed from Teflon but of a contrasting color to that of the cutting block 20. The button 24 also is formed with a concave depression in its upper surface, the radius of curvature of the depression being less than that of the concave depression 22 in the block 20. Thus, when button 24 is properly positioned in the block 20 as shown in FIG. 2, a double curve is formed to receive the donor corneal tissue (not shown). This construction will assure proper central positioning of the donor tissue in the cutting block 20.

The neck 16 on stand 14 is bored to form a cylindrical passageway 26 that accomodates a removable piston indicated generally by the reference numeral 28 that is used to drive the trephine 30 through the donor tissue. Passageway 26 also positively positions the piston 28 and the trephine 30 so that the trephine will move along a defined path to assure an accurate and central cut of the donor tissue positioned on the cutting block 20.

Piston 28 includes a bushing 32 that fits slideably in the cylindrical passageway 26 in the neck 16 of stand 14. Bushing 32 has an integrally formed collar 33 that rests on top of the neck 16 to position the bushing 32 and limit the downward movement of the piston 28. An arbor 34 has an upper portion 36 that is slideably received inside of bushing 32 with a coil spring 38 seated inside of bushing 32 and exerting force on the bottom edge of the central portion 36 to bias the arbor 34 upwardly. A removable collar 40 is affixed to the arbor 34 beneath the bushing 32 with a set screw 42 holding the collar 40 in place. Collar 40 therefore limits the upward movement of the arbor 34 against the bias of the spring 38.

The lower end of the arbor 34 is formed with a plurality of progressively smaller outside diameters and a plurality of vertical slits around its circumference to provide an expanding collet 44. The different diameters of the collet 44 will accommodate trephines 30 of different diameters within the range of 6.2 mm to 10.0 mm. These are the trephines that are presently commonly used so that the donor tissue can be cut to the desired size.

Received inside the arbor 34 is an expander 46 which has a conical-shaped lower end 48 and an enlarged central portion 50 that is threaded to match threads tapped inside the upper end 36 of the arbor 34. As best seen in FIG. 2, the expander 46 is threaded into the arbor 34 with the conical-shaped end 48 extending into the collet 44. Thus, as the expander 46 is turned, it will advance downwardly permitting the conical-shaped end 48 to expand the collet 44 and thereby grip and hold the selected trephine 30.

To facilitate the turning of the expander 46 there is provided a knob 52 having a central vertical opening 58 which receives the upper end of the expander 46. A set screw 54 will lock the knob 52 and expander 46 together so that when the knob 52 is turned, the expander 46 will also turn. Preferably, the exterior circumferential surface of the knob 52 is knurled to facilitate its turning.

To assemble the piston 28, the spring 38 is dropped into the bushing 32 and the arbor 34 positioned in and through the bushing 32 with the collar 40 extending beneath the bushing 32. The collar 40 is then positioned around the lower end of the arbor 34 above the collet 44 and the set screw 42 tightened to lock the arbor 34 in place relative to the bushing 32. Of course, the arbor 34 can be depressed against the bias of spring 38, but the collar 40 will limit any upward movement of the arbor 34 relative to the bushing 32 thus assuring that the upper end 36 will always remain positioned inside of the bushing 32.

The expander 46 is then threaded inside of the arbor 34, and the knob 52 placed on top of the expander 46 with its lower portion 56 extending over the upper end 36 of the arbor 34. The set screw 54 is then tightened to lock the knob 52 onto the expander 46.

Figure 3:
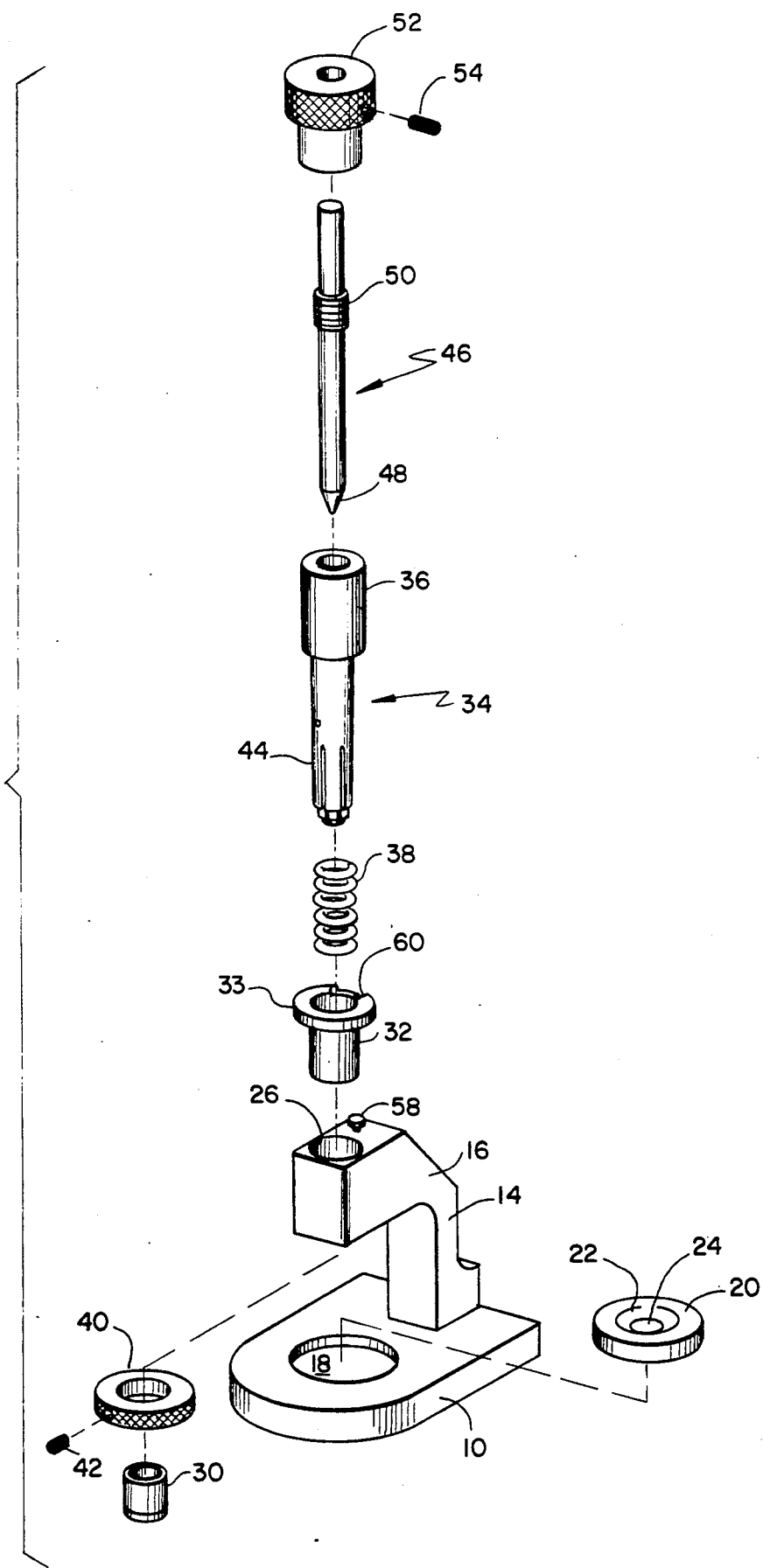
FIG. 3 is an exploded perspective view of the device of the invention.

The entire assembly of the knob 52, expander 46, arbor 34 and bushing 32 is then inserted through the passageway 26 in the neck 16 of stand 14. In order to hold this piston assembly 28 in place, there is provided a locking lug 58 in the top surface of the neck 16 just adjacent the passageway 26. The collar 33 of the bushing 32 is then formed with a cut-out portion 60 (FIG. 3) so that when the piston assembly 28 is inserted into the passageway 26 with the cut-out portion 60 aligned with the locking lug 58, the piston assembly 28 can be fully inserted in the passageway 26 until the collar 33 is seated on the neck 16. At this time, the collar 33 is turned slightly so that it will be engaged beneath the locking lug 58 and held in place by it.

In use, the donor tissue is placed endothelium side up and centered over the guide button 24 in the cutting block 20. The cutting block 20 is then placed and positioned in the circular depression 18 in the base 10. A trephine 30 of the desired size is then placed on the lower end of the collet 44 and is locked in place by holding the collar 40 while turning the knob 52 thereby turning the expander 46 and moving the conical-shaped lower end 48 downwardly to expand the collet 44 and thereby grip the trephine 30. With the piston assembly 28 locked in place in the stand 14 and held there by the locking lug 58 as previously described, force is applied to the top of the knob 52 thereby moving the arbor 34 with the trephine 30 held by collet 40 downwardly to cut the donor button. Once the donor button is properly cut, force is released from the knob 52 to allow the piston assembly 28 to slowly return to its initial position by force of the spring 38. Preferably, the surgeon will gradually release the force on the knob 52 to allow the piston assembly 28 to return slowly to its original position since fast elevation increases the chance of the donor button remaining in the trephine 30. However, to minimize this possibility, the groves in the collet 44 prevent the creation of a vacuum during trephination which further decreases the chance of the donor button becoming trapped within the trephine 30.

From the foregoing description, it will be evident that the device of the invention provides quick, easy and accurate cutting of donor tissue to the desired diameter of the donor button to be transplanted. Since the cutting block 20 is positively positioned in the stand 14 directly centered beneath the piston assembly 28, accurate central cutting of the donor tissue will be assured because of the circular depression 22 and guide button 24 in the cutting block 20. Preferably, the components of the device of the invention are made of stainless steel so that they can be sterilized in an autoclave or sterilized with gas. The parts are precisely machined so that movement of the piston assembly 28 will be straight and accurate in all instances. The entire piston assembly 28 can be quickly and easily removed from the stand 14 by merely turning the assembly to release it from the locking lug 58.

Have thus described the invention in connection with a preferred embodiment thereof, it will be evident to those skilled in the art that various revisions and modifications can be made to the preferred embodiments disclosed herein without departing from the spirit and scope of the invention. It is my intention, however, that all such revisions and modifications as are obvious to those skilled in the art will be included within the scope of the following claims.

What is claimed is as follows:

1. A press for the trephination of donor tissue used in corneal transplants by use of a trephine, said press comprising a support stand and a piston assembly movable relative to the support stand for controlled movement along a precisely defined path, the piston assembly having means for holding the trephine and thereby moving the trephine along the defined path during the trephination, said means including an expandable collet having a shoulder engageable by the trephine for positively gripping and maintaining the trephine in a selected position, and means for positively positioning and holding the donor tissue in said defined path so that the trephine will be accurately centered over the donor tissue to produce an accurate and central cut of the donor tissue when the piston assembly moves the trephine along the defined path.

2. The press of claim 1 in which there is provided spring means to bias the piston assembly away from the donor tissue, the piston assembly being moveable against the bias of said spring means.

3. The press of claim 2 in which the collet has a plurality of shoulders so as to accommodate trephines of different sizes.

4. The press of claim 3 in which the means for holding the donor tissue includes a cutting block, and the support stand has means for positively holding the cutting block in the defined path.

5. The press of claim 4 in which the cutting block has a concave central depression and a removable central portion in the center of the depression, the central portion having a concave upper surface the curvature of which has a smaller radius of curvature than the concave depression.

6. The press of claim 5 in which the piston assembly includes an arbor, the support stand has an opening for receiving and guiding the arbor along the defined path, and the expandable collet is positioned at the lower end of the arbor.

7. The press of claim 6 in which the arbor has a central passageway, and an expander is received and movable in said passageway to expand the collet.

8. The press of claim 1 in which the collet includes a plurality of slots that provide for expansion of the collet, said slots also preventing the creation of a vacuum during trephination of the donor tissue.

9. A press for the trephination of donor tissue used in corneal transplants by use of a trephine, said press comprising first means for holding a trephine during the trephination, second means for controllably moving the trephine along a precisely defined path, the second means including a support stand and a piston assembly movable relative to the support stand, the piston assembly including the first means for holding the trephine, third means for holding the donor tissue including a cutting block having a concave central depression and a removable central portion in the center of the depression, the central portion having a concave upper surface the curvature of which has a smaller radius of curvature than the concave depression, and fourth means including a portion of the support stand for positively positioning and holding the cutting block in the defined path so that the trephine will be accurately centered over the donor tissue to produce an accurate and central cut of the donor tissue when the second means moves the trephine along the defined path.

10. The press of claim 9 in which the piston assembly includes as expandable collet for releasably holding the trephine.

11. The press of claim 10 in which the piston assembly includes an arbor, the support stand has an opening for receiving and guiding the arbor along the defined path, and the collet is positioned at the lower end of the arbor.

12. The press of claim 11 in which the arbor has a central passageway, and an expander is received and movable in said passageway to expand the collet.

13. The press of claim 12 in which the collet includes a plurality of slots that provide for expansion of the collet, said slots also preventing the creation of a vacuum during trephination of the donor tissue.

* * * * *